(12) United States Patent
Tolmosoff

(10) Patent No.: US 9,135,403 B1
(45) Date of Patent: Sep. 15, 2015

(54) APPARATUS AND METHOD FOR STORING AND DISPENSING PHARMACIST-FILLED PRESCRIPTION MEDICATIONS

(71) Applicant: John Tolmosoff, Madera, CA (US)

(72) Inventor: John Tolmosoff, Madera, CA (US)

( * ) Notice: Subject to any disclaimer, the term of this patent is extended or adjusted under 35 U.S.C. 154(b) by 0 days.

(21) Appl. No.: 14/446,292

(22) Filed: Jul. 29, 2014

(51) Int. Cl.
*G07F 11/62* (2006.01)
*G06F 19/00* (2011.01)
*G07F 17/00* (2006.01)
*G07F 11/16* (2006.01)

(52) U.S. Cl.
CPC ............ *G06F 19/3462* (2013.01); *G07F 11/62* (2013.01); *G07F 17/0092* (2013.01); *G07F 11/165* (2013.01)

(58) Field of Classification Search
CPC .... G07F 17/0092; G07F 11/58; G07F 11/165
See application file for complete search history.

(56) References Cited

U.S. PATENT DOCUMENTS

| | | | |
|---|---|---|---|
| 5,385,265 A * | 1/1995 | Schlamp | 700/237 |
| 6,170,929 B1 * | 1/2001 | Wilson et al. | 700/243 |
| 6,464,142 B1 * | 10/2002 | Denenberg et al. | 235/462.46 |
| 6,694,217 B2 * | 2/2004 | Bloom | 700/215 |
| 7,123,989 B2 * | 10/2006 | Pinney et al. | 700/237 |
| 7,194,333 B2 * | 3/2007 | Shoenfeld | 700/243 |
| 7,383,099 B2 * | 6/2008 | Pollard et al. | 700/232 |
| 8,121,725 B2 * | 2/2012 | Baker et al. | 700/236 |
| 8,954,190 B2 * | 2/2015 | Braunstein | 700/242 |

* cited by examiner

*Primary Examiner* — Timothy Waggoner
(74) *Attorney, Agent, or Firm* — Richard A. Ryan

(57) ABSTRACT

An apparatus and method that simplifies the process of storing and dispensing prescription medications for both the patient and the pharmacy. The apparatus has a housing enclosing a conveying assembly that conveys a plurality of bins. A package containing prescription medication prepared and filled by a pharmacist is placed in one bin. Electronic tags on the packages and bins are read by an electronic reader to position the bins inside the housing. The customer reaches into the housing to grab the package or a grabbing mechanism grabs the correct package and drops it in a tray that is accessed by the customer. A display screen displays information and allows the customer to enter a code to obtain the medication. Cameras and other security equipment ensures the correct person obtains the medication. A computer in the housing controls the operation of apparatus and contacts the customer that the medication is ready.

14 Claims, 13 Drawing Sheets

APPARATUS AND METHOD FOR STORING AND DISPENSING PHARMACIST-FILLED PRESCRIPTION MEDICATIONS

CROSS-REFERENCE TO RELATED APPLICATIONS

None.

STATEMENT REGARDING FEDERALLY SPONSORED RESEARCH

Not Applicable.

REFERENCE TO A SEQUENCE LISTING, A TABLE OR A COMPUTER PROGRAM LISTING APPENDIX SUBMITTED ON A COMPACT DISC

Not Applicable.

BACKGROUND OF THE INVENTION

A. Field of the Invention

The field of the present invention relates generally to storing and then dispensing prescription medications to customers or patients of a pharmacy or other organization that supplies prescription medications to such persons. In particular, the present invention relates to apparatuses and methods that are utilized to store and dispense prescription medications that have been filled by a pharmacist or the like. Even more particularly, this invention relates to such apparatuses and methods that allow the customer or patient to obtain his or her prescription medications without requiring direct contact with the pharmacist.

B. Background

Nearly everyone who has been ill or who has health conditions or any health related issues that require treatment to cure and/or control the progression of the health issue has been prescribed medication, generally referred to herein as prescription medications. As well known in the art, the process of prescribing and dispensing prescription medications are closely controlled by various federal and/or state laws to prevent such medications from being prescribed to persons unless authorized by a doctor, nurse practitioner or other medical professional and being dispensed to persons who were not prescribed the medications by an appropriate medical professional. Most people obtain their prescription medications from a pharmacist, or someone employed by or under the supervision of a pharmacist, who works at a pharmacy. The pharmacy may be a stand-alone facility or, often more common, it may be located in a store or market, hospital or other medical services building, nursing home or other facility that provides pharmaceutical and non-pharmaceutical products or services. With regard to pharmacies that are located inside a store, the store may be a drug store, grocery store, general store or market or the like. Because of convenience and other personal considerations, many people prefer to utilize a pharmacy that is located in a store in which they can engage in other shopping activities so they can shop in the store while they wait to get their prescription medication.

The typical process for a person to obtain a prescription medication, after the medication has been prescribed by an appropriate medical professional, is to take the prescription to a pharmacy, provide the prescription to an employee of the pharmacy to have the prescription filled and pay for the medication, wait while the prescription is filled by a licensed pharmacist or someone under his or her direction, go to a counter or other location to obtain the prescription medication from the pharmacist or other pharmacy employee. More recently, the prescription may be emailed, faxed or otherwise forwarded to the desired pharmacy directly by the medical professional's office and the person only has to go there to pick up and pay for the medication. Even with the advent of forwarding a patient's prescription directly to the pharmacy, the wait time for a person to obtain his or her prescription medication can be somewhat lengthy. In part, the customer's wait time is affected by the number of people in line to get their own prescription medications filled, the limited number of pharmacy employees available to assist persons and fill the prescriptions and the time it takes the pharmacist to carefully and properly prepare the medication and fill the prescription. As well known in the art, the process of filling the prescription requires the pharmacist or an employee working for or with the pharmacist to place the medication in the appropriate container (often a bottle), label the container with the patient's name and medication information and placing the container in a bag, sack or like carrying container.

Because the process of obtaining prescription medication from a pharmacy or like facility can take a somewhat significant amount of time, many people have their prescriptions forwarded directly to the pharmacy and then time their trip to the pharmacy when they think the medication will be prepared and ready for pick up. Alternatively, the patient will personally drop off the prescription at the pharmacy and then he or she returns to the pharmacy at a later time to pick up their medication. Although generally more time efficient than waiting at the pharmacy for the prescription to be filled, this process requires a second trip to the pharmacy and then waiting in line to pick up the medication. To reduce the amount of wait time for the customer after the prescription medication is ready, some pharmacies will contact the customer via telephone, email or text when his or her prescription medication is ready to be picked up.

Even though some of the above processes do reduce the wait time associated with filling a person's prescription, there is generally little being done in the way of reducing the time it takes the person to pick up and pay for his or her prescription medication after it has been filled by the pharmacist. As well known, when the person gets to the pharmacy he or she will have to wait in line behind other persons who are picking up their prescription medication or transacting other business with the pharmacy, including dropping off their prescription, discussing their prescription medication with the pharmacist, asking questions regarding prescription and non-prescription medications and the like. Any of these or other issues can result in the pharmacy's customer having to wait, often for a relatively long time, to get to the front of the line to pick up and pay for his or her prescription medication. Some pharmacies have a drive-up window that allows the customer to pull up to the window and remain in his or her vehicle, as opposed to going into the store, to obtain and pay for the prescription medication. Although this avoids the time required for the customer to park the vehicle and go into and walk through the store (typically the pharmacy is located in the back of the a grocery, drug or other stores), it does not reduce the waiting time required to for the pharmacy employee to have time to assist a particular pharmacy customer. Often the amount of time a customer has to wait in line to be assisted by a pharmacy employee can be quite frustrating, particularly if the customer is only needing to pick up and pay for his or her prescription medication and he or she must wait on other people having lots of questions or other issues (which may include, but is not limited to, payment or insurance issues). In addition to customer frustration, the pharmacist and his or her employees may feel somewhat pressured to hurry up when dealing with the customers at the counter or in line at the drive up window, which can result in mistakes and/or making the pharmacy customer feel like he or she is not important to the pharmacy.

A number of apparatuses, systems and methods exist that attempt to speed up the delivery of previously filled prescription medications to pharmacy customers. One very common system utilizes a plurality of open bins that are designated with letters and/or numbers to receive prescription medications therein that are then associated with a particular patient. In one example, the pharmacy may have one bin for each letter of the alphabet (i.e., 26 bins) and will put a bag or sack having filled prescription medication(s) therein in the bin that matches the first letter of the patient's last name. While some pharmacies will utilize fewer bins by combining together two or more less common letters for last names, others will use more bins by further narrowing the range of last names that go into the bin. When the pharmacy customer, who may be the patient to which the medication was prescribed or someone on his or her behalf, comes to the pharmacy to pick up the prescription medication, he or she will give the patient's last name to the pharmacy employee at the counter or drive-up window. The employee will then go to the bin associated with the patient's name, look through the bin to find the correct package containing the medication for that specific patient and retrieve the patient's bag, sack or other package from the bin. After obtaining confirming information from the customer regarding the patient to make sure he or she has the correct package, the employee will look at or electronically scan the package for the price of the medication, convey the price information to the customer and then obtain payment from the customer. After the medication has been paid for by the customer, the pharmacy employee will hand the package to the customer. As one would expect, the above process of obtaining the prescription medication can take some time and has significant potential for errors. Even if the pharmacy has a separate pick-up counter or window, if a person is in line waiting for their turn to tell the employee the patient's name, the wait could be somewhat long if each person ahead of them has to go through the same process. In addition, if the patient has a common last name, it is possible that the pharmacy employee will have to check several times to make sure he or she has the prescription medication for the correct patient before handing the package over to the customer picking up the package. This double checking adds to the time required for the pharmacy to obtain and present the prescription medication to the customer and, despite the best efforts of the pharmacy, can still result in medication being given to the wrong person.

A number of machines have been developed to assist in the process of filling prescription medications. Generally, these machines are configured to automatically fill the bottle or other container with the medication from sources of medications stored inside the machine to mechanize, and presumably quicken, the pharmacist's process of taking stock medicines and then filling the container with the appropriate (i.e., prescribed) amount of medication. Examples of such machines, as well as methods of filling prescription medications, are set forth in U.S. Publication No. 2011/0172815 to Kim, U.S. Pat. No. 8,478,441 to Liguori, et al., U.S. Publication No. 2013/0104499 to Moncrief, et al., U.S. Publication No. 2009/0240528 to Bluth, U.S. Pat. No. 4,518,208 to Marder, U.S. Pat. No. 7,228,198 to Vollm, et al., U.S. Pat. No. D190,902 to Brewer, Intl Publication No. WO 2009/115985 to Liguori, et al. and Intl Publication No. WO 2013/119646 to Cashman, et al. Although several of these machines do deliver the prescription medication to the patient, they are configured as a kiosk that is visually and/or audibly connected to a doctor who prescribes the medication via the kiosk and the machine then fills the prescription while the patient is at the kiosk. In effect, these kiosks eliminate the pharmacist. While this may be suitable for certain areas of the United States or elsewhere in the world where doctors and/or pharmacists are not widely available, they are not likely to be suitable to most areas of the United States and the more "developed" countries which require separation between the doctor and the pharmacy and require medications to be filled by a pharmacist.

What is needed, therefore, is an improved apparatus and method for dispensing prescription medication to a patient, either directly or through a person on his or her behalf, after a prescription has been filled by a pharmacist or a pharmacist employee. The improved apparatus and method should simplify and speed up the process for the customer to pick-up and pay for the prescription medication after it has been filled by the pharmacist. Preferably, the improved apparatus and method should eliminate the need for the customer picking up the prescription medication to go to the counter or window of a pharmacy, wait in a line, provide name information to the pharmacy employee, wait while the employee finds the prescription medication, pay the employee for the prescription and receive the prescription medication from the employee. Such an improved apparatus and method should be configured to be able to receive, store and dispense prescription medications for customers of a pharmacy after the prescriptions have been filled by a pharmacist. Preferably, the new apparatus and method for obtaining prescription medications will include various safeguards to ensure that only the person who was prescribed the medication, or a person who has authority to pick up the medication on his or her behalf, obtains the prescription medication from the new apparatus and while using the new method. The new apparatus and method should be configured to be utilized by a wide variety of different types of locations that have a pharmacy which fills and dispenses prescription medications.

SUMMARY OF THE INVENTION

The apparatus and method for storing and dispensing pharmacist-filled prescription medications of the present invention provides the benefits and solves the problems identified above. That is to say, the present invention is an improved apparatus and method of storing and dispensing prescription medication after a patient's prescription was filled by a pharmacist pursuant to a prescription that was identified by a doctor as being necessary for the patient. The apparatus and method of the present invention significantly simplifies and speeds up the process for a customer to pick-up and pay for prescription medication after it has been filled by the pharmacist. In a preferred embodiment of the present invention, the improved apparatus and method eliminates the need for most customers to go to a counter or window of a pharmacy to pick up a prescription medication, where the customer would typically have to wait in a line, provide name information to the pharmacy employee, wait while the employee locates the prescription medication, pay the employee for the prescription and receive the prescription medication from the employee. The improved apparatus and method of the present invention is configured to receive, store and dispense prescription medications for customers of a pharmacy after the prescriptions have been filled by a pharmacist. To ensure that only the patient who was prescribed the medication, or a person who has authority to pick up the medication on the patient's behalf obtains the prescription medication from the apparatus and method of the present invention, the new apparatus and method for obtaining prescription medications includes a number of safeguards to verify and track who uses the apparatus. The new apparatus and method is adaptable for use by a wide variety of different types of locations that have a pharmacy which fills and dispenses prescription medications, including drug stores, grocery stores and the like.

In a preferred aspect of the present invention, the apparatus for storing and dispensing prescription medication in a package after the prescription medication has been prepared by a pharmacist or an employee of a pharmacy generally comprises a housing having a conveying assembly and a prescription identification system disposed in the housing and a customer access panel on the front of the housing. The housing has a front side, a back side, top end, bottom end, a first side and a second side with at least a front wall at the front side, a first side wall at the first side, a second side wall at the second side and a top wall at the top end. The housing defines an interior area therein. The conveying assembly comprises a plurality of bins that are moveably disposed inside the interior of the housing so as to move along a conveying path. Each of the bins has a compartment that is sized and configured to receive the package containing the prescription medication. Preferably, the apparatus has one or more doors at either the front side or the back side of the housing, depending on where the apparatus will be placed in the pharmacy. The doors are configured to allow the pharmacist or employee to access the interior area of the housing and place the package having the prescription medication on one of the bins in the interior area of the housing. The prescription identification system is associated with the conveying assembly to controllably position the bin having the package and to assist in removing the correct package from the bin. In a preferred embodiment, the prescription identification system has an electronic reader configured to detect and read identifier tags on each of the bins and an electronic tag on the package containing the prescription medication. The customer access panel has a computer and a display screen and/or a keypad that is electronically connected to the computer. The customer access panel operates the conveying assembly to move the prescription medication to the prescription tray so the prescription medication may be retrieved by the customer of the pharmacy.

In one embodiment, the prescription tray is the bin having the package and it is positioned by the conveying assembly behind an aperture in the front wall or the doors, if at the front side of the apparatus, that has a flap associated the aperture. The customer, who is either the patient or a person who has permission from the patient to get the prescription medication from the pharmacy, puts his or her hand through the flap and the aperture to get the package. In another embodiment, the apparatus has a grabbing mechanism that is structured and arranged to remove the package containing the prescription medication from one of the bins and place the package in a prescription tray which is accessible by a customer of the pharmacy. In a preferred embodiment, the grabbing mechanism has a conveyor with grabbing device attached there to move the grabbing device to the bin having the package. The grabbing device is configured to grab the package in the bin and place the package on or in a prescription tray. The prescription tray can open outward of the housing to allow the customer to access the prescription tray for removing the prescription medication from the apparatus. In another embodiment, the grabbing mechanism and the prescription tray are disposed in an extension housing located at the top end of the apparatus that extends outward from the front side of the housing. In this embodiment, the extension housing has an opening therein to allow the customer to access the package on the prescription tray.

Accordingly, the primary aspect of the present invention is to provide a new apparatus and method for storing and dispensing prescription medications that has the advantages discussed above, as well as elsewhere in the present disclosure, and which overcomes the various disadvantages and limitations associated with prior art apparatuses and methods for storing and dispensing prescription medications.

It is an important aspect of the present invention to provide a new apparatus and method for storing and dispensing prescription medications that is structured and arranged to receive such medications after they have been filled by a pharmacist, store the medications and then dispense the medications to a patient or his or her authorized representative after he or she has paid for the medications at the apparatus.

It is also an important aspect of the present invention to provide a new apparatus and method for storing and dispensing prescription medications that simplifies and speeds up the process for a customer, whether the patient or a person on his or her behalf, to pick-up and pay for prescription medication after it has been filled by the pharmacist.

It is also an important aspect of the present invention to provide a new apparatus and method for storing and dispensing prescription medications that at least generally eliminates the need for most customers to go to a counter or window of a pharmacy to pick up prescription medication that has been filled by a pharmacist.

Another important aspect of the present invention is to provide a new apparatus and method for storing and dispensing prescription medications that includes a number of safeguards which ensure only the patient who was prescribed the medication, or a person who has authority to pick up the medication on his or her behalf, obtains the prescription medication from the new apparatus and while using the new method.

Yet another important aspect of the present invention is to provide a new apparatus and method for storing and dispensing prescription medications that is configured to be utilized by a wide variety of different types of locations that have a pharmacy which fills and dispenses prescription medications.

As will be explained in greater detail by reference to the attached figures and the description of the preferred embodiment which follows, the above and other aspects are provided or accomplished by the present invention. As set forth herein and will be readily appreciated by those skilled in the art, the present invention resides in the novel features of form, construction, mode of operation and combination of processes presently described and understood by the claims. The description of the invention which follows is presented for purposes of illustrating one or more of the preferred embodiments of the present invention and is not intended to be exhaustive or limiting of the invention. The scope of the invention is only limited by the scope of the claims which follow after the discussion.

BRIEF DESCRIPTION OF THE DRAWINGS

In the drawings which illustrate the preferred embodiments and the best modes presently contemplated for carrying out the present invention.

DETAILED DESCRIPTION OF THE PREFERRED EMBODIMENTS

With reference to the figures where like elements have been given like numerical designations to facilitate the reader's understanding of the present invention, the preferred embodiments of the present invention are set forth below. The enclosed text and drawings are merely illustrative of one or more preferred embodiments and, as such, disclose one or more different ways of configuring the present invention. Although specific components, materials, configurations and uses are illustrated, it should be understood that a number of variations to the components and to the configuration of those components described herein and in the accompanying figures can be made without changing the scope and function of the invention set forth herein. For instance, although the figures and description provided herein set forth certain shapes and configurations and describe certain materials for the apparatus of the present invention, those skilled in the art will readily understand that these are shown and described merely for exemplary purposes and to simplify this disclosure and that the present invention is not so limited.

Figure 1:
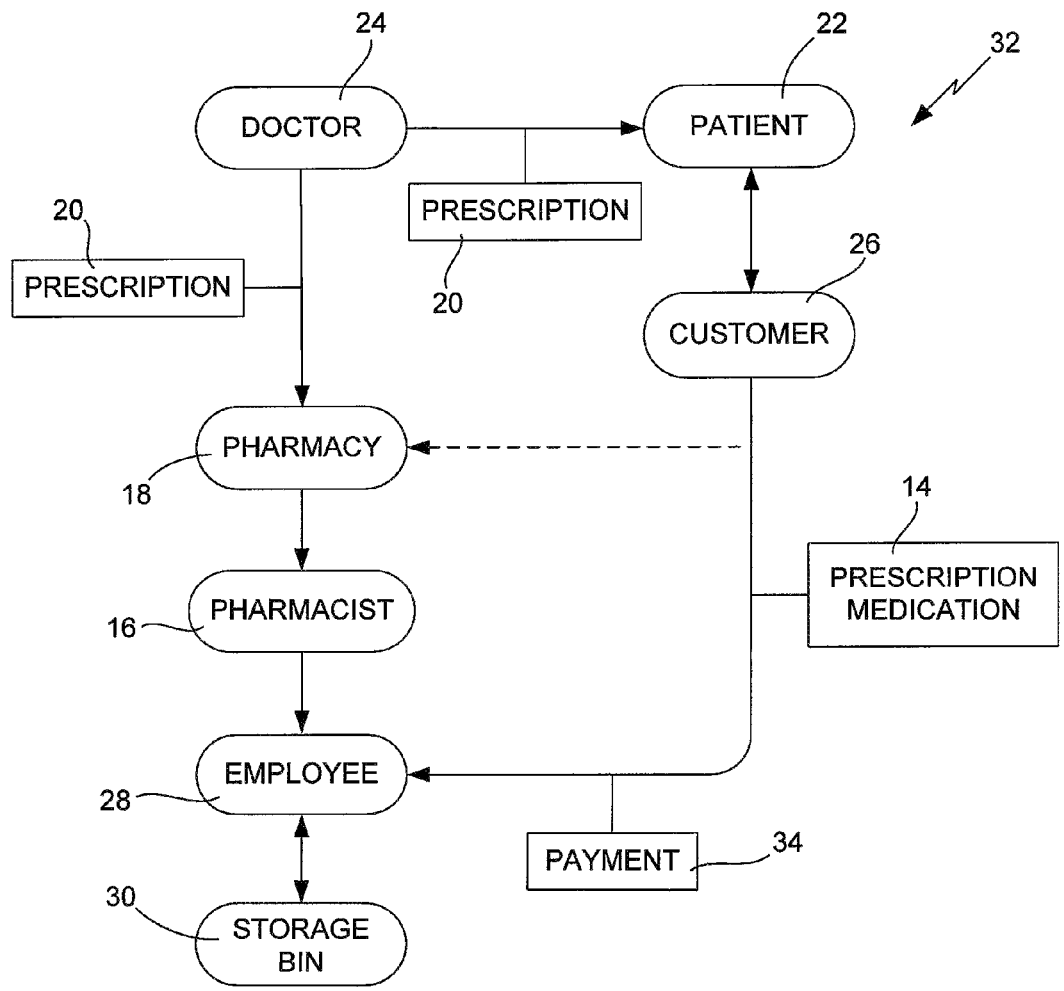
FIG. 1 is a flow chart generally showing a prior art method for a patient to obtain prescription medications from a pharmacy having a pharmacist and other employees who fill and assist the patient with getting the prescription.

An apparatus that is configured pursuant to various embodiments of the present invention is shown generally as 10 in the FIGS. 2-7 and 13-17. A method of using the apparatus 10 of the present invention is shown generally as 12 in FIGS. 4 and 14. As is set forth in more detail below, the apparatus 10 of the present invention is utilized to store and dispense prescription medications 14 that are filled by a pharmacist 16, typically at a pharmacy 18 in a drug store, grocery store, market, hospital, nursing home or the like, according to a prescription 20 prescribed for a patient 22 by a doctor or other medical professional 24, as shown in the prior art chart FIG. 1. Often, as shown in FIG. 1, the prescription 20 is sent directly to the pharmacy 18 by fax, email or phone for preparation. Alternatively, the patient 22 or someone acting on his or her behalf, will take the prescription to the pharmacy 18. The person dealing with the pharmacy 18, whether the patient or his or her representative, is shown as the customer 26 in FIG. 1. Typically, the prescription medication 14 is prepared by the pharmacist 16 according to the prescription 20 and placed, either by the pharmacist 20 or another employee 28 of the pharmacy 18 in an open storage bin 30 (usually with the medication 14 inside of a bag or other package). A common prior art method, shown as 32 in FIG. 1, of dispensing prescription medications 14 utilizes a plurality of open storage bins 30 in the pharmacy 18 that are each designated with letters and/or numbers to receive prescription medications 14 associated with a particular group of patients, such as persons who last name start with the same letter. When the customer 26 goes to the pharmacy 18 to pick up the prescription medication 14, he or she will give the patient's last name to an employee 28 at the counter or drive-up window. The employee 28 will then go to the storage bin 30 associated with the patient's name, look through the particular storage bin 30 to find the correct package containing the medication 14 for the patient 22 and then retrieve the patient's bag, sack or other package from the bin 30. After obtaining confirming information from the customer 26 regarding the patient 22 to make sure the employee 28 has the correct package, the employee 28 will look at or electronically scan the package for the price of the medication 14, convey the price information to the customer 26 and then obtain payment 34 from the customer 26. After the medication 14 has been paid for by the customer 26, the pharmacy employee 18 will hand the package to the customer 26. As known by persons who have been customers 26, this process can sometimes take a frustratingly long amount of time. As set forth below, the apparatus 10 and method 12 of the present invention solves the various problems associated with the prior art method 32.

Figure 2:
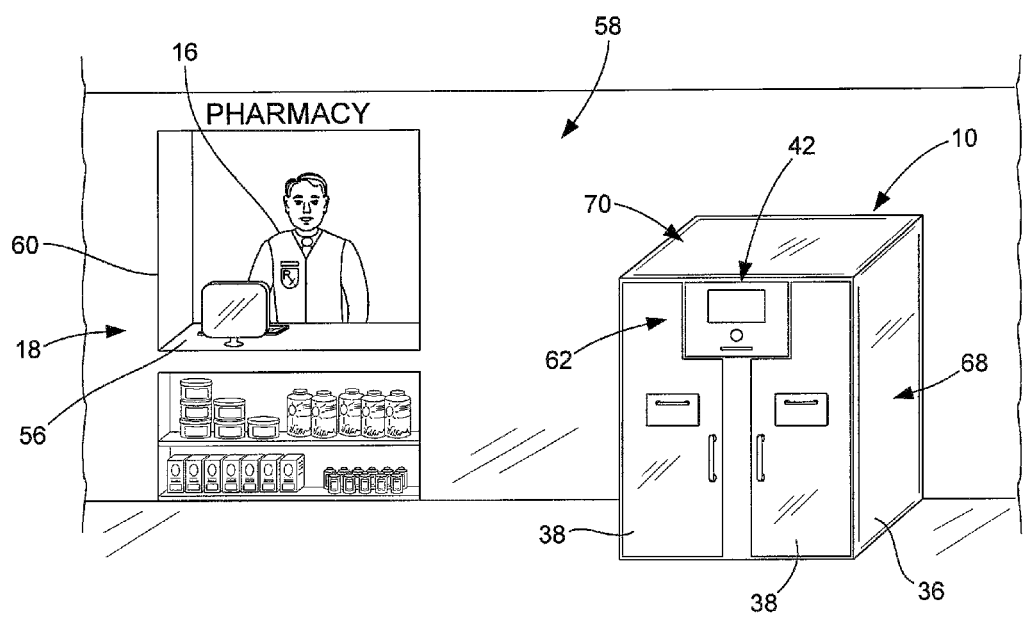
FIG. 2 is a side perspective view of a first embodiment of an apparatus for storing and dispensing prescription medications that is configured according to one of the preferred embodiments of the present invention shown sitting on the floor in front of a wall near a pharmacy.
Figure 3:
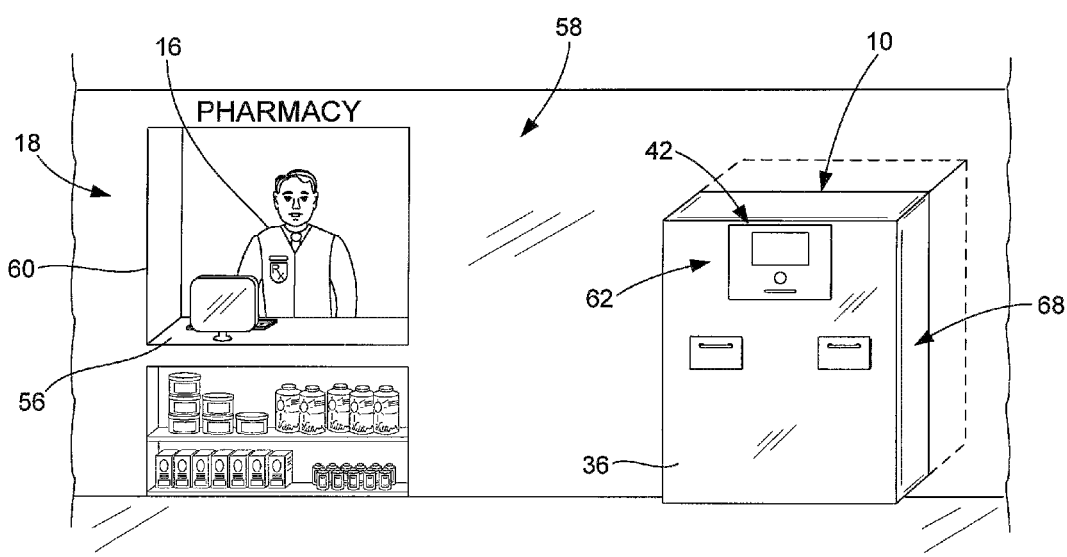
FIG. 3 is a side perspective view of a second embodiment of an apparatus for storing and dispensing prescription medications that is configured according to one of the preferred embodiments of the present invention shown with the apparatus in a wall of a pharmacy.
Figure 4:
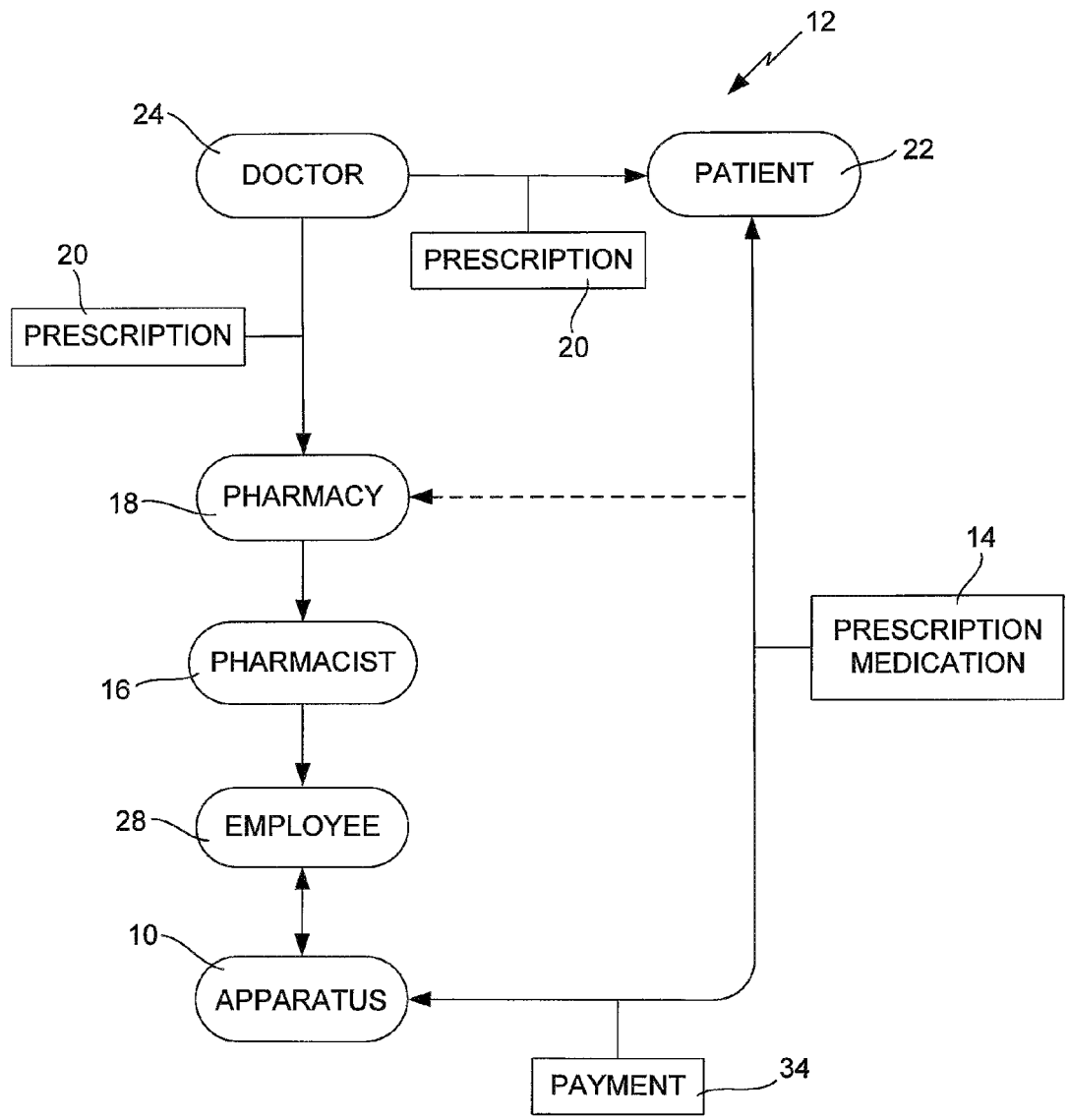
FIG. 4 is a flow chart generally showing a method that is configured according to one embodiment of the present invention for a patient to obtain prescription medications from a pharmacy having a pharmacist and other employees who fill and assist the patient with getting the prescription.

The apparatus 10 of the present invention generally comprises a housing 36, one or more doors 38 allowing access to an interior area 40 of the housing 36, a customer access panel or module 42, a conveying assembly 44 having one or more bins 46 for receiving and storing bags or other packages 48 of prescription medication 14, a prescription identification system 50 for identifying which package 48 is associated with the customer 26 and a grabbing mechanism 52 configured to remove the desired package 48 from the bin 46 and place the package in a prescription tray 54 where it can be retrieved by the customer 26. As will be readily appreciated by persons skilled in the art, the apparatus 10 eliminates the need for the customer 26 to go to the pharmacy counter, shown as 56, to take the time to interact with the pharmacist 16 or employee 28 in order to pay for and obtain the prescription medication 14 for the patient 22 (which may also be the customer 26). A summarized version of the method 12 of the present invention using apparatus 10 is shown in FIG. 4. In the embodiment of FIG. 2, the apparatus 10 is located outside of the pharmacy 18, typically in a store of some kind with the pharmacy 18 being a separate, securely closeable area of the store, against a wall 58 near the customer service window 60. In the embodiment of FIG. 3, the apparatus 10 is embedded in the wall 54, much like an ATM machine. As will be described in more detail below, packages 48 of prescription medication 14 are placed inside on of the bins 46 in the interior area 40 of the apparatus 10 through the doors 38. In the embodiment of FIG. 2, the doors 38 are located on and form part of the front wall 62 of the housing 36. In the embodiment of FIG. 3, the doors are located on the back wall 64 of the housing 36, as specifically shown in FIG. 13. Together, the front wall 62, back wall 64, first side wall 66, second side wall 68, top wall 70 and bottom wall 72 (best shown in FIGS. 5-7) enclose interior 40 and the various components therein.

The various walls 62-72 of the housing 36 can be made out of a wide variety of different materials, including metal, composites, plastics, wood and the like. Generally, however, the materials for the housing 36 should be selected to be sufficiently rigid and strong to service the purposes and accomplish the objects set forth herein (including being strong enough to prevent easy entry into the interior 40 by a thief or other unauthorized person). Typically, materials utilized for ATM machines, vending machines and kiosks will be suitable for the housing 36 of the apparatus 10. The doors 38 will be pivotally attached to one or more walls of the housing 36 using standard hinges 74, such as those shown in FIG. 13.

Figure 13:
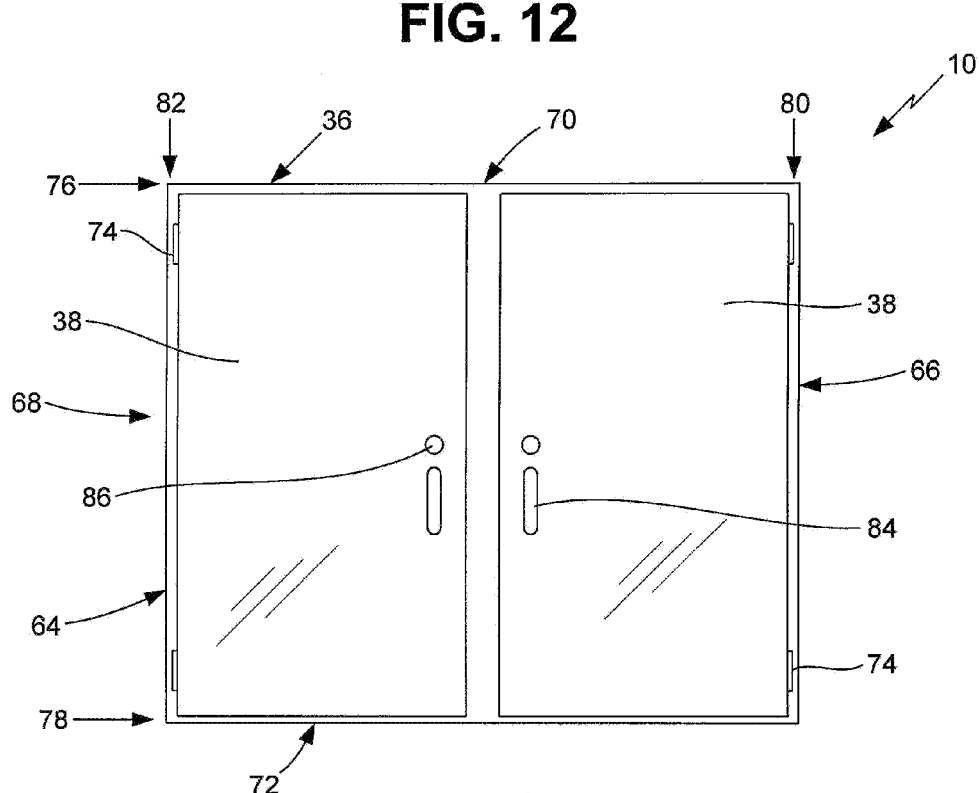
FIG. 13 is a back view of the apparatus of FIG. 3 showing the doors located inside the pharmacy.

In the embodiment shown in the figures, the customer access panel 42 will be generally located near the top end 76 of the housing 36 so it is at or near eye level for the customer 26 and the prescription tray 54 will be located generally mid-way between the top end 76 and the bottom end 78 where access will be more convenient for the customer's hands. The hinges 74 for the doors 38 will be generally at or near the first side 80 and the second side 82 of the housing 36, as shown in FIG. 13. Each of the doors 38 will have a handle 84 associated therewith to allow the pharmacist 16 or an employee 28 to access the interior 40 of the housing 36 to place packages 48 of prescription medication 14 in the bins 46 of the conveying assembly 44. Each door 38 will have a locking mechanism 86 to secure the prescription medications 14 inside the interior 40 of the housing 36 so they will not be improperly accessed by customers 26 or unauthorized persons. To assist with access to the prescription medications 14 in the prescription tray 54 by the customer 26, the prescription tray 54 should also have a handle 88 thereon. In one of the preferred embodiments of the present invention, the prescription tray 54 is of the pull-down type of drawer that is commonly utilized in certain vending machines to obtain product and at the post office or other postal services to drop off larger sized packages. The configuration and use of handles 84/88, locking mechanisms 86 and prescription trays 54 are generally well known in the art.

Figure 5:
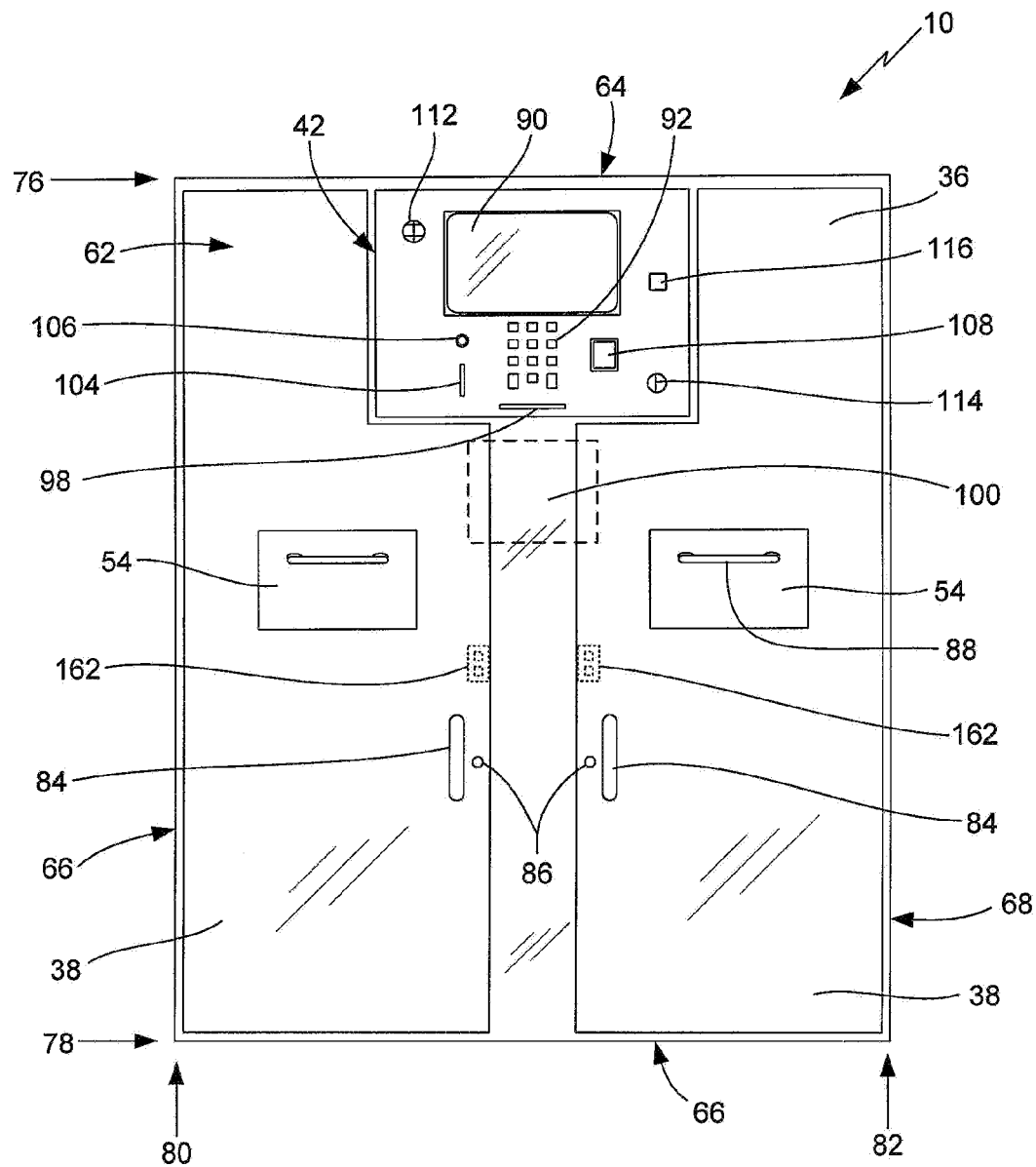
FIG. 5 is an enlarged front view of the apparatus of FIG. 2.
Figure 12:
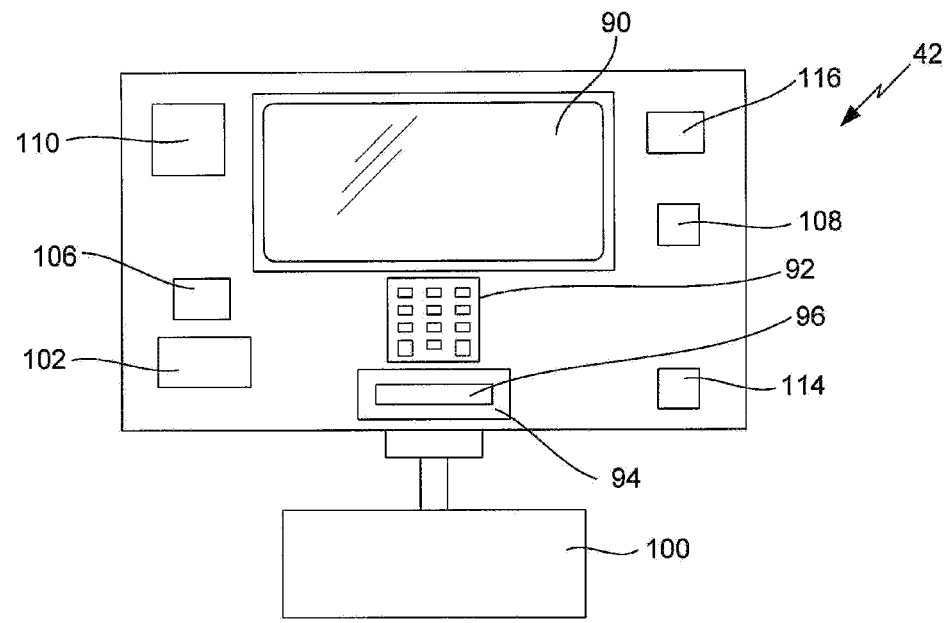
FIG. 12 is a back view of the control module and computer module shown in FIGS. 2 and 3.

The customer access panel or module 42 is structured and arranged for use by the customer 26 when he or she wants to obtain prescription medication 14 from a previously filled prescription 20. A wide variety of customer-friendly access components can be utilized with the apparatus 10 and method 12 of the present invention. As will be readily appreciated by those skilled in the art, the customer access panel/module 42 can be configured as an integral panel with the front wall 62 (likely preferred) or one of the side walls 66/68 of the housing 36. In an alternative embodiment, the customer access panel/module 42 of the apparatus 10 can be configured as a removable module. This may be preferred because of the ability to easily remove and replace a module if any of the components fail to perform as required. For purposes of hereinafter describing this component of the present invention, the term "panel" will refer to either a fixed, integral panel or a replaceable module. Preferably, the customer access panel 42 at least comprises a touch-type display screen 90, a numeric or alphanumeric keypad 92, a printer 94 having a roll of paper 96 to eject a confirmation receipt out of a paper slot 98 and a computer board or panel 100, as best shown in FIGS. 5 and 12. As well known in the art, the display screen 90 is utilized to display information to the customer 26 and, when using the touch screen type, allow the customer 26 to enter data that is processed by the computer 100 to operate the conveying assembly 44, prescription identification system 50, the grabbing mechanism 52 and the components of the customer access panel 42.

In a preferred embodiment, the customer access panel 42 also has a card reader 102 that reads a credit card or other identification and/or payment card that is inserted into a card slot 104, as shown in FIGS. 5 and 12. For security and identification purposes, the customer access panel 42 of apparatus 10 also has a video (preferred) or photographic camera 106 that records customers 26 and other persons who use the apparatus 10 to obtain a prescription medication 14 in case verification of the identity of the customer 26 or other person is necessary later. If desired, the customer access panel 42 can include a thumb print reader 108 that either allows or requires the customer 26 to have his or her thumb print read before being able to access the display panel 90 or operate the conveying assembly 44. The customer access panel 42 can also include an alarm mechanism 110 that is connected to speaker 112 to emit a loud siren-type signal if anyone is tampering with the apparatus 10 or if one or more of the verification steps set forth below do not result in proper verification. For purposes of the present invention, the use of the card reader 102, camera 106, thumb print reader 108 and/or alarm mechanism 110 are referred to herein, whether used collectively or singularly, as security components. The security components are utilized to prevent customers 26 from obtaining prescription medications 14 without paying for them and to prevent other persons from having unauthorized access to the prescription medications 14 that are stored in the interior 40 of the housing 36.

In a preferred embodiment of the apparatus 10 of the present invention, the customer access panel 42 also includes a number of customer convenience components. These components include the speaker 112 described above, a microphone 114 and a motion detector 116. In addition to its use for the alarm function, the speaker 112 can be utilized to broadcast audio commands to the customer 26 regarding what he or she should do to retrieve and pay for his or her prescription medication 14. The microphone 114 can be utilized to allow the customer 26 to speak his or her commands to the apparatus 10 instead of utilizing the touch-screen display screen 90 and/or the keypad 92. The computer 100 could include programming that allows the customer 26 to speak and hear commands in a wide variety of different languages and dialects. The customer 26 can choose the language using the display screen 90 or keypad 92. If desired, the apparatus 10 could be configured to "recognize" the customer 26, typically via his or her credit or other card that is inserted into the card slot 98, to automatically default to the customer's language preference. The motion detector 116 can be utilized to detect when a person, whether or a customer 26 or not, approaches the front of the apparatus 10. The apparatus 10 can activate the display screen 90 and put forth a visual and/or an audio welcoming message to the person. In addition, detection of a person approaching the apparatus 10 can also activate the camera 106 to begin taking video and/or still photos of the person as a form of additional security in case that information is needed later to assist in the investigation of a crime, such as theft from or damage to the apparatus 10.

Figure 6:
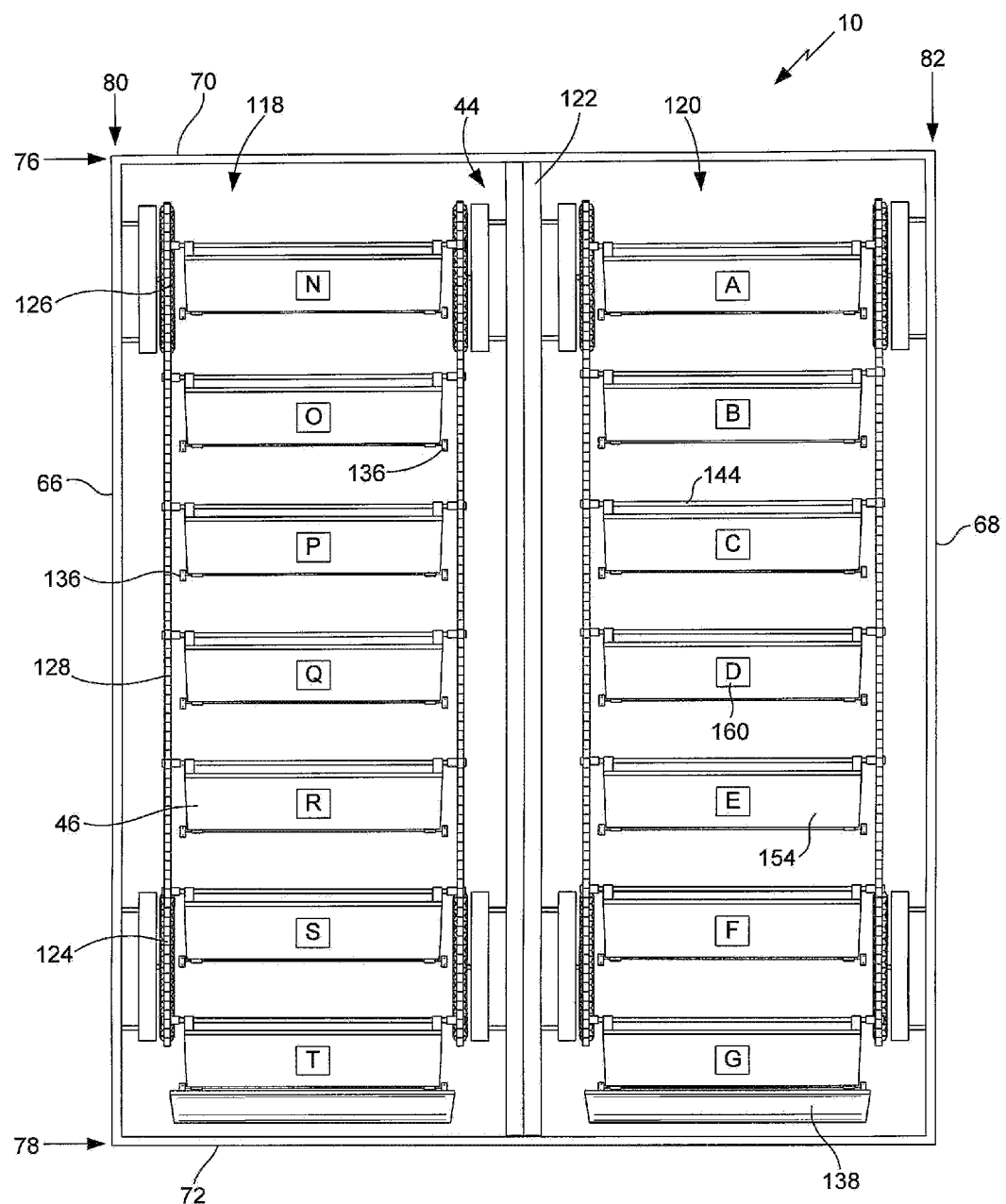
FIG. 6 is a front view of the apparatus of FIG. 5 with the doors of the apparatus open to shown the conveying assembly having a plurality of bins for storing prescription medications.
Figure 7:
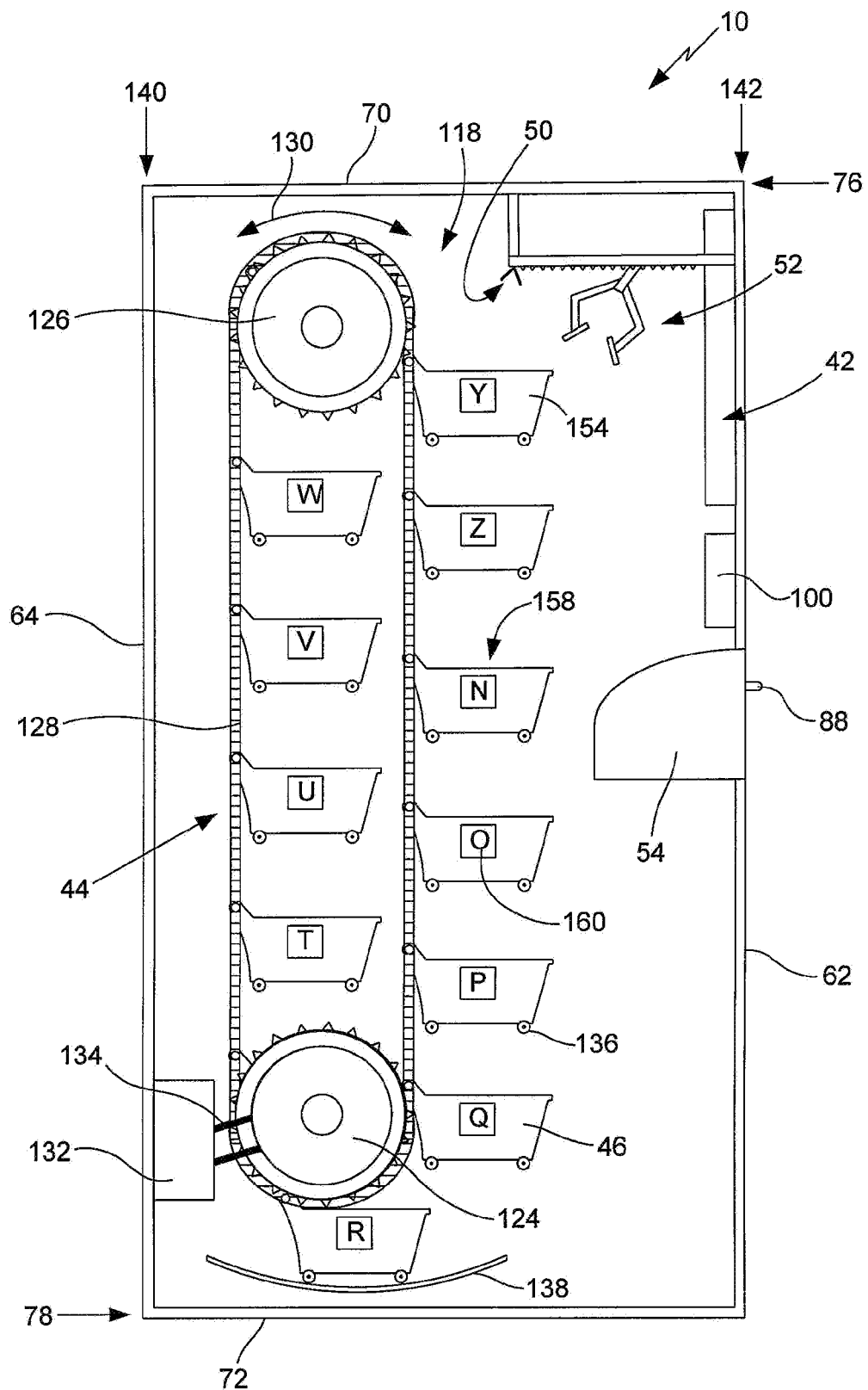
FIG. 7 is a left side view of the apparatus of FIG. 6 with the side wall removed to show the conveying assembly inside the housing of the apparatus and the prescription tray that receives the patient's prescription.

The conveying assembly 44, located inside housing 36 of apparatus 10, is utilized to move one of the bins 46 into a desired position, whether for a pharmacist 16 or an employee 28 to place one or more prescription medications 14 in the bin 46 or for a customer 26 to obtain his or her prescription medication 14. In a preferred embodiment, the conveying assembly 44 comprises a plurality of bins 46, as best shown in FIGS. 6 and 7, that are conveyed in a generally oval path inside the housing 36. In the embodiments shown in the figures, the bins 46 are separated into two conveying subassemblies, shown as a left subassembly 118 and a right subassembly 120 in FIG. 6, that are separated by one or more vertical frame members 122. In the present configuration, both subassemblies 118/120 are virtually identical with regard to their structure and function. The bins 46 are each separately identified. In the present embodiment, the bins 46 are each labeled with one letter of the alphabet, with the letter representing the first letter of the patient's 22 last name. In the embodiment shown in the figures, subassembly 118 has letters N through Z and subassembly 120 has letters A through M. The conveying assembly 44 also comprises a chain and socket mechanism having a first or lower socket 124, a second or upper socket 126 and a drive chain 128 that interconnects the two sockets 124/126 as they move along a conveying path 130, as best shown in FIGS. 6 and 7. Each subassembly 118/120 has a pair of sockets 124/126 and a drive chain 128, as best shown in FIG. 6. In the embodiment shown in FIGS. 6 and 7, the lower socket 124 is connected to a motor 132, via a motor belt 134, to be the driving socket, as best shown in FIG. 7. Each bin 46 is connected to the pair of drive chains 128 in the respective subassembly 118/120, in a manner that keeps the bins 46 substantially level as they move along the conveying path 130. Each bin 46 has one or more wheels 136 on the bottom surface thereof that are positioned to engage a skid plate 138. In the embodiment shown in the figures, each of the subassemblies 118/120 are disposed generally toward the back side 140 of the apparatus 10, with the prescription identification system 50, grabbing mechanism 52 and prescription tray 54 being located at or toward the front side 142 of the apparatus 10, as best shown in FIG. 7. As will be readily appreciated by persons skilled in the art, the drive chain 128 may be a belt or like device and the motor belt 134 may be a chain or the like.

Figure 8:
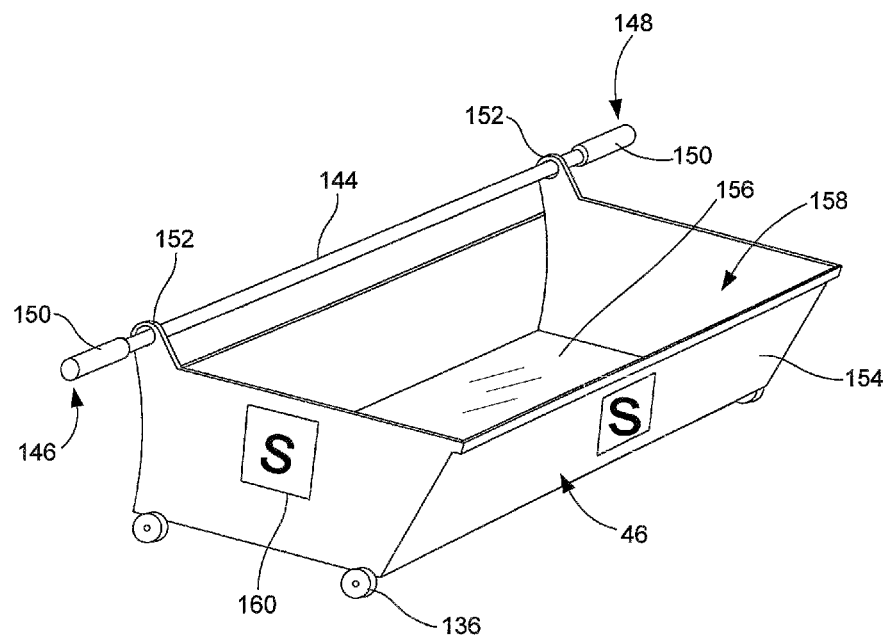
FIG. 8 is a side perspective view of one of the bins of the conveying assembly of FIGS. 7 and 8 showing the support rod received through the hangers of the bin.

Each bin 46 is connected to and conveyed by the drive chain 128. In a preferred embodiment, drive chain 128 comprises a plurality of interconnected chain links and each bin 46 is attached to a pair of opposing chain links by a support rod 144 having a first end 146 and a second end 148, as best shown in FIGS. 6 and 8. A sleeve 150 at each end 146/148, which are best shown in FIG. 8, allows the bin 46 to pivot as it moves along the conveying path 130 so that the bin 46 will remain substantially level and not dump the prescription medications 14 that are placed therein. As best shown in FIG. 8, rod 144 is received through hangers 152 at the back of the bin 46. Depending on the shape of the bins 46, each bin 46 has one or more side walls 154 and a bottom wall 156 that define a open receiving compartment 158 in which packages 48 of prescription medications 14 are placed inside by a pharmacist 16 or employee 28 and removed therefrom by the grabbing mechanism 52 when the customer 26 uses apparatus 10 to retrieve and pay for his or her prescription medication 14. Each bin 46 has one or more identifier tags 160 associated therewith that help the pharmacist 16 or employee 28 place prescription medications 14 in the bin 46 and which work with the prescription identification system 50 to identify the location of the package 48 containing the prescription medication sought by the customer 26. To assist with loading the bins 46 with packages 48 of prescription medication 14, the conveying assembly 44 also has a pair of operating devices 162 associated with each of the subassemblies 118/120 that allow the pharmacist 16 or employee 28 to initiate movement of the bins along the conveying path 130 so he or she may position the desired bin 46 at a location where it is more convenient for him or her to place the packages 48 in the correct bin 46. In a preferred embodiment, the operating devices 162 are buttons, with one button configured to move the bins 46 upward and one button configured to move the bins 46 downward along conveying path 130. As will be readily known by those skilled in the art, various other devices can be used for operating devices 162 to permit manual operation of the conveying assembly 44.

Figure 10:
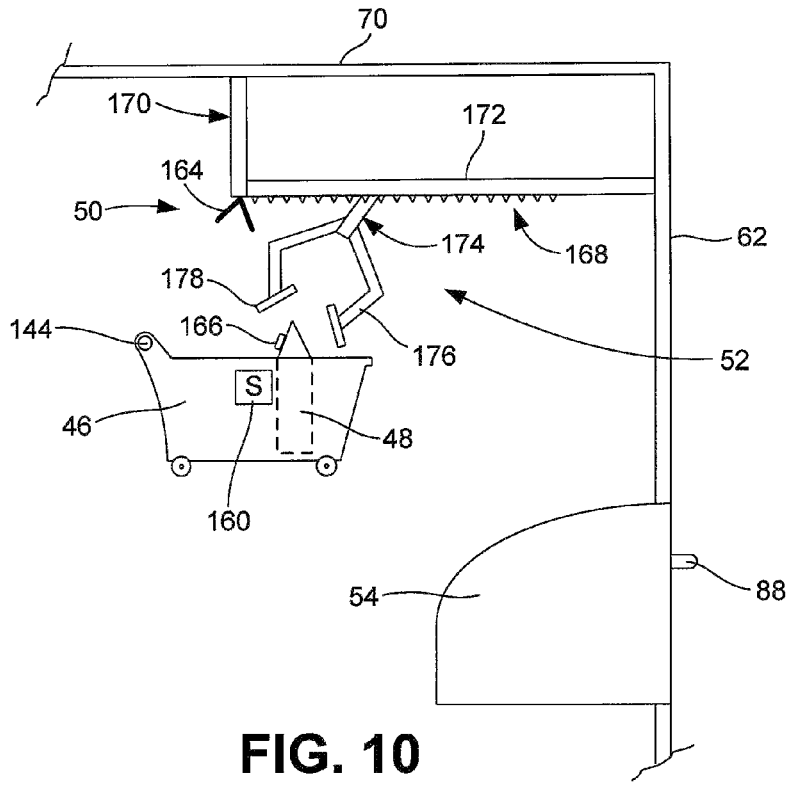
FIG. 10 is a left side view of one of the bins, shown separate from the conveying assembly, having a prescription bag therein that is about to be grabbed by the prescription grabbing mechanism of the identification and selection system of the apparatus of the present invention to place the prescription bag in the prescription tray.
Figure 11:
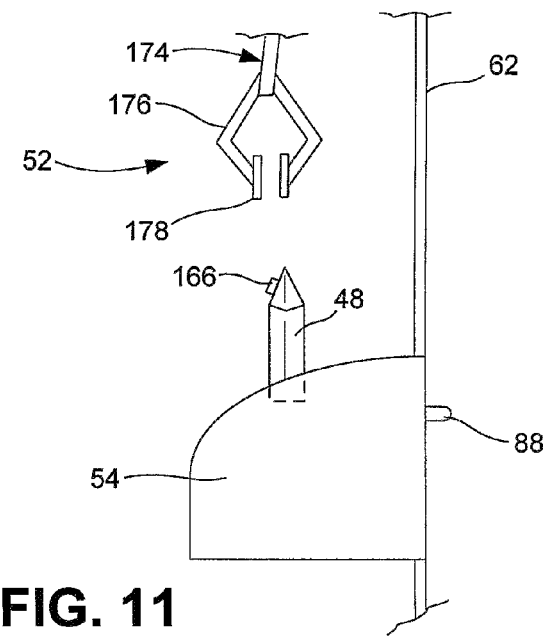
FIG. 11 is a left side view of the prescription bag and grabbing mechanism of FIG. 10 after the prescription bag was placed in the prescription tray for retrieval by the patient/customer.

The prescription identification system 50 is utilized to verify that the packages 48 are placed in the proper bin 46 and to automatically position the appropriate bin 46, which is the bin 46 having the package 48 containing the prescription medication 14 desired by the customer 26, at the location where the package 48 can be retrieved by the grabbing mechanism 50 and placed in the prescription tray 54 for retrieval by the customer 26, as best shown in FIGS. 7, 10 and 11. The prescription identification system 50 of the apparatus 10 generally comprises an electronic reader 164 mounted inside the interior 40 of the housing 36 for each of the subassemblies 118/120 and a plurality of electronic tags 166, with each package 48 having one unique electronic tag 166 associated therewith, such as attached at or near the top of the package 48, as best shown in FIGS. 7, 10 and 11. In the embodiments shown in the figures, the electronic reader 164 is mounted to a support frame 168, having one or more frame members 170, that is disposed in the interior 40 of the housing 36, as best shown in FIG. 10. The identifier tags 160 on the bins 46 are also used as part of prescription identification system 50. In use, the prescription identification system 50 is utilized to make sure the packages 48 are placed in the proper bin 46, to position a specific bin 46 for access by the grabbing mechanism 52 and to identify which package 48 is needed by the customer 26.

In general, the use of electronic tags and devices configured to read those tags in combination with products and items associated with products, such as pallets and the like, have recently become popular for purposes of store inventory, theft control and automated checkout. Although there are a variety of different types of electronic tags, one of the most common types are magnetic strips that contain information which is read by the electronic reader 164. Perhaps the smallest and generally most available and cost effective type of electronic tag is that which is known as a radio-frequency identification (RFID) tag. As generally known by those familiar with the technology, RFID technology utilizes radio waves to exchange data between an electronic tag attached to or embedded in an object and a reader configured to read the electronic tag for purposes of identifying and/or tracking the product. Through use of RFID tags, manufacturers or others can give each product its own unique identifying number. RFID tags have an integrated circuit for storing and processing information and for modulating and demodulating a radio-frequency signal ("RF") and an antenna for receiving and transmitting the RF signal. RFID tags can be either passive, active or battery assisted passive and, depending on configuration, can be read from a distance of several meters or more away. Passive RFID tags have no battery and are generally the least expensive. Active RFID tags have a battery that allows the RFID tag to broadcast its signal. Battery assisted passive RFID tags have a small battery that allows the RFID tag to be activated when in the presence of an appropriately configured RFID reader.

Figure 9:
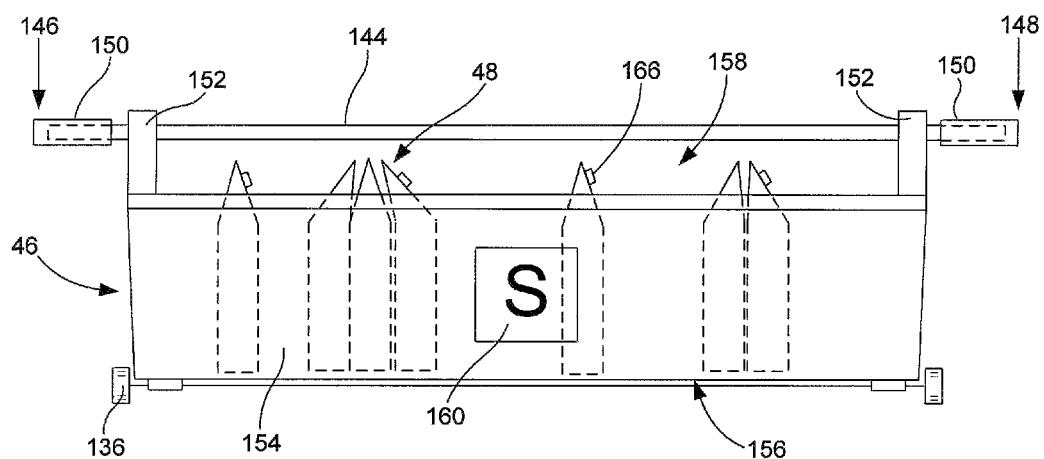
FIG. 9 is a front view of the bin of FIG. 8 shown with prescription bags in the bin compartment.

With regard to the prescription identification system 50 of the present invention, an electronic tags 166 (which are shown enlarged in the figures for ease of labeling) are placed on each package 48 when the prescription medication 14 is prepared by the pharmacist 16. After the pharmacist 16 or an employee 28 places the packages 48 in the bins 46, the conveying assembly 44 can be run to allow the electronic reader 164 to verify that each package is placed in the proper bin 46, which can be done by comparing the electronic tag 166 on the packages 48 to the identifier tags 160 on the bins 46. When the customer 26 enters his or her information to receive the prescription medication 14, the conveying assembly 44 will convey the bins 46 along the conveying path 130 until it recognizes the bin 46 having that is associated with the patient 22 (and therefore the package 48 having the prescription medication 14). When this bin 46 is at the appropriate position, the conveying mechanism 44 will stop to allow the grabbing mechanism 52 to grab the package 48 containing the prescription medication 14. As shown in FIG. 9, there is typically a plurality of packages 48 in a bin 46. The electronic reader 164 will scan the packages 48, identify the proper package 48 and then direct the grabbing mechanism 52 to that package 48. As set forth below, the grabbing mechanism 52 will then move into position and grab the customer's package 48 and drop it in the prescription tray 54 so he or she can retrieve the package 48 from the apparatus 10, as shown in FIGS. 10 and 11.

The grabbing mechanism 52 comprises a grabbing conveyor 172 that moveably mounts a grabbing device 174 to the support frame 168 to generally move the grabbing device 174 from the front side 142 of the apparatus 10 towards the back side 140 to retrieve a customer's package 48 from the bin 46 in which the package 48 is located, as shown in FIGS. 10 and 11. The grabbing device 174 comprise one or more arms 176 and a pair of clamps 178 that work together to clamp onto or otherwise engage the package 48 that is associated with a patient 22 that is being retrieved by a customer 28. If desired, one or more magnets can be utilized to assist with grabbing the package 48 to retrieve the package 48 from the bin 46 where the package 48 has been stored while waiting for the customer 26 to pick up. As will be readily appreciated by those skilled in the art, a wide variety of different types of grabbing mechanisms 52 can be utilized with the apparatus 10 of the present invention. These grabbing mechanism 52 may utilize different devices to grab onto and securely hold a package 48 while the package 48 is moved from the compartment 158 of a bin 46 to the prescription tray 54.

As will be readily appreciated by those skilled in the art, the method 12 of storing and dispensing pharmacist-filled prescriptions of the present invention utilizes the apparatus 10 described above to store and dispense prescription medication 14 to a customer 26 so he or she will not be required to wait in a line at the counter 56 of the pharmacy 18 to obtain the prescription medication 14. The doctor 24, or someone in his or her office, will transfer the prescription 20 to a pharmacy 18 for preparation and filling or the patient 22 himself or herself will take the prescription 20 to the pharmacy 18 for preparation and filling. The pharmacist 16 at the pharmacy 18 will prepare the prescription medication 14 according to the prescription 20 and place the prescription medication 14 in a package 48. The package 48 will be labeled with the patient's name, the medication and other information, which will be associated with an electronic tag 166 that is either already on the package 48 or which is applied to the package 48 by the pharmacist 16 or an employee 28 of the pharmacy 18. An electronic code 179 will be assigned to the package 48 and the code 180 will be transmitted to the patient 22 with a message letting him or her know the prescription medication 14 is ready for pick up at the pharmacy 18. The pharmacist 16 or an employee 28, which is likely to be more typical, will unlock the appropriate lock 86 on the doors 38 of apparatus 10, use the operating devices 162 to move the appropriate bin 46 to a position where it is easy to put the package 48 in the compartment 158 of the bin 46, place the package 48 containing the patient's prescription medication 14 in the appropriate bin 46 according to the identifier tag 160 on the bins 46 (i.e., a bin 46 having an identifier tag 160 with the first letter of the patient's last name) and then close and lock the door 38. Typically, multiple packages 48 will be placed in the apparatus 10 at the same time. If a package 48 is in the wrong bin, which is determined by comparing the electronic tags 166 to the identifier tags 160, then an alarm will sound via the speaker 112 to inform the employee 28 of the error. If desired, the customer access panel 42 can be configured to display an error message on the display screen 90 telling the employee 28 where the incorrect package 48 was placed. Once the package 48 is in the apparatus 10, the computer 100 can call, email, text or otherwise contact the patient 22 to let him or her know the medication 14 is ready to be picked up at the pharmacy 18.

Figure 14:
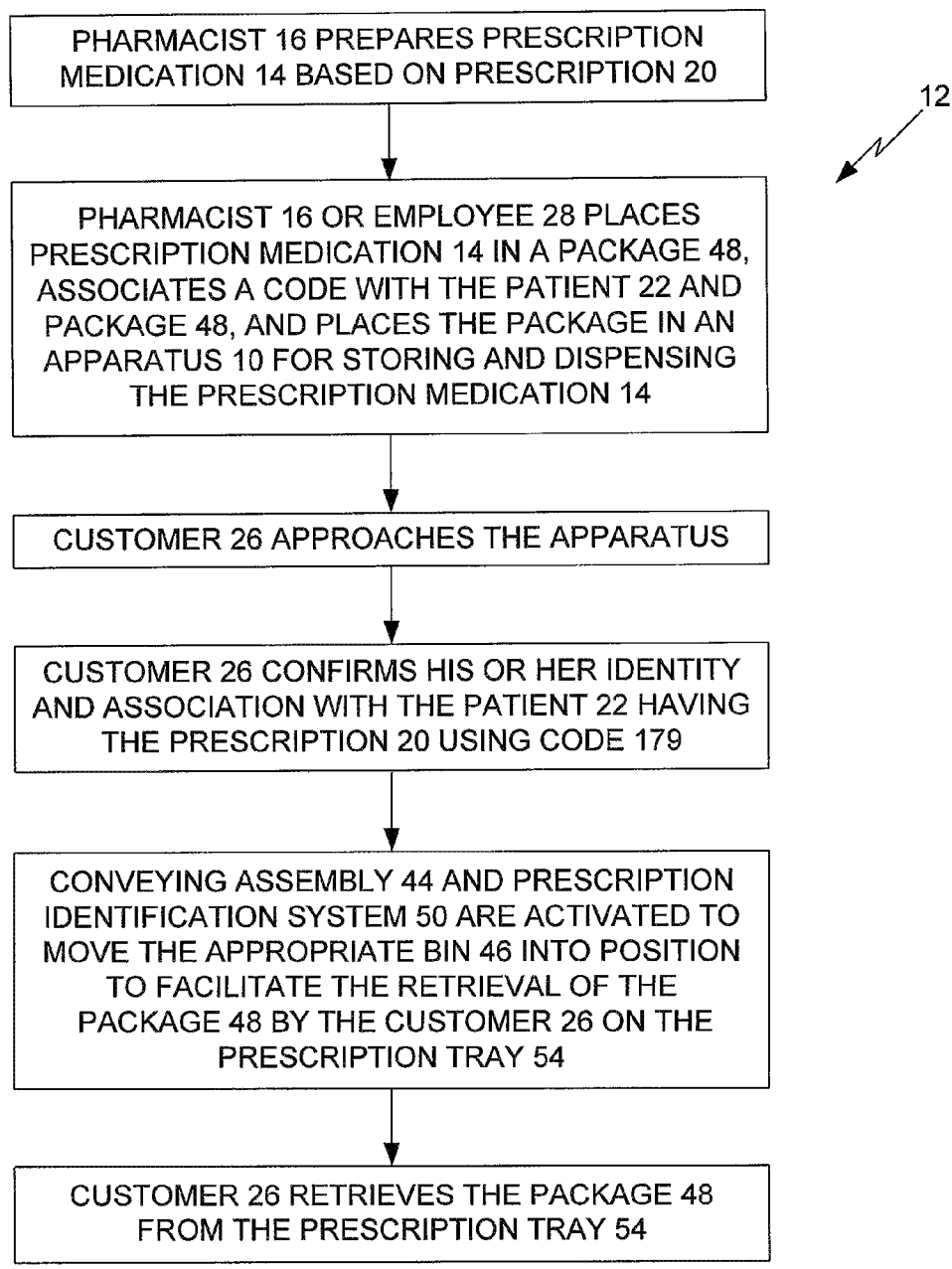
FIG. 14 is a flow chart showing a method configured according to one of the preferred embodiments of the present invention.

According to the method 12 of the present invention, which is set forth in FIG. 14, when the customer 26 comes to the pharmacy 18 to get his or her prescription medication 14, he or she will go to the apparatus 10 instead of the window 60. The motion detector 116 will activate or turn on the apparatus 10 and provide a greeting for the customer 26 welcoming him or her to the apparatus 10. The user will insert his or her credit card or an identification card into the card slot 104 where it will be read by the card reader 102 and enter the electronic code 179 when prompted by the display screen 90 and/or an audible message from the speaker 112. The electronic code 179 can be entered via the keypad 92, on the touch display screen 90 or by speaking the code 179 into the microphone 114. Once the computer 100 has verified that the correct customer 26 is there, then the conveying assembly 44 will be activated to move the bins 46 along the conveying path 130. The electronic reader 164 of the prescription identification system 50 will scan the identifier tags 160 on the bins 46 and position the appropriate bin 46 at a location where the grabbing mechanism 52 can retrieve the package 48 from the bin 46. The grabbing device 174 will grasp the package 48, raise it out of the compartment 158 of the bin 46, move the package 48 to the prescription tray 54 and then place the package 48 in the prescription tray 54. The electronic reader 164 will ensure that the correct package 48 was grabbed before dropping the package 48 into the prescription tray 54. The customer 26 then opens the prescription tray 54 by pulling on the handle 88 thereof, or the computer 100 will automatically open the prescription tray 54 for the customer 54. A paper receipt will be printed by the printer 94 and ejected out the paper slot 98. If desired, an electronic receipt can also be emailed or texted to the patient 22 verifying that the prescription medication 14 was dispensed. The camera 106 will record video and/or photographs of the customer 26 using the apparatus 10 in case there is an issue later of an inappropriate person obtaining the prescription medication 14. As will be readily appreciated by those skilled in the art, the apparatus 10 and method 12 of the present invention will simplify and speed-up the process by which a customer obtains prescription medication 14. In addition, the apparatus 10 and method 12 of the present invention will lessen the work load for the pharmacist 16 and his or her employees 28.

Figure 15:
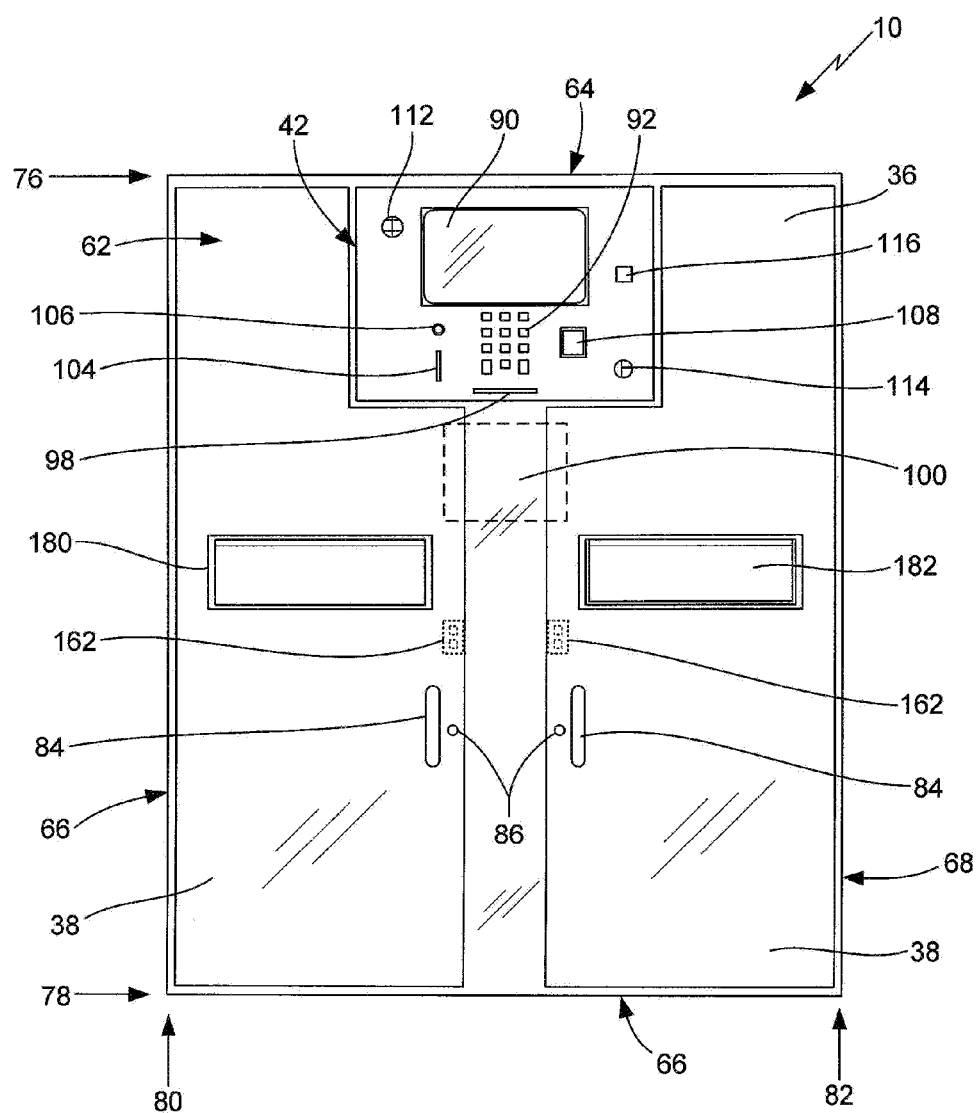
FIG. 15 is a front view of a third embodiment of the apparatus of the present invention showing use of an access aperture and flap to retrieve the prescription medication.
Figure 16:
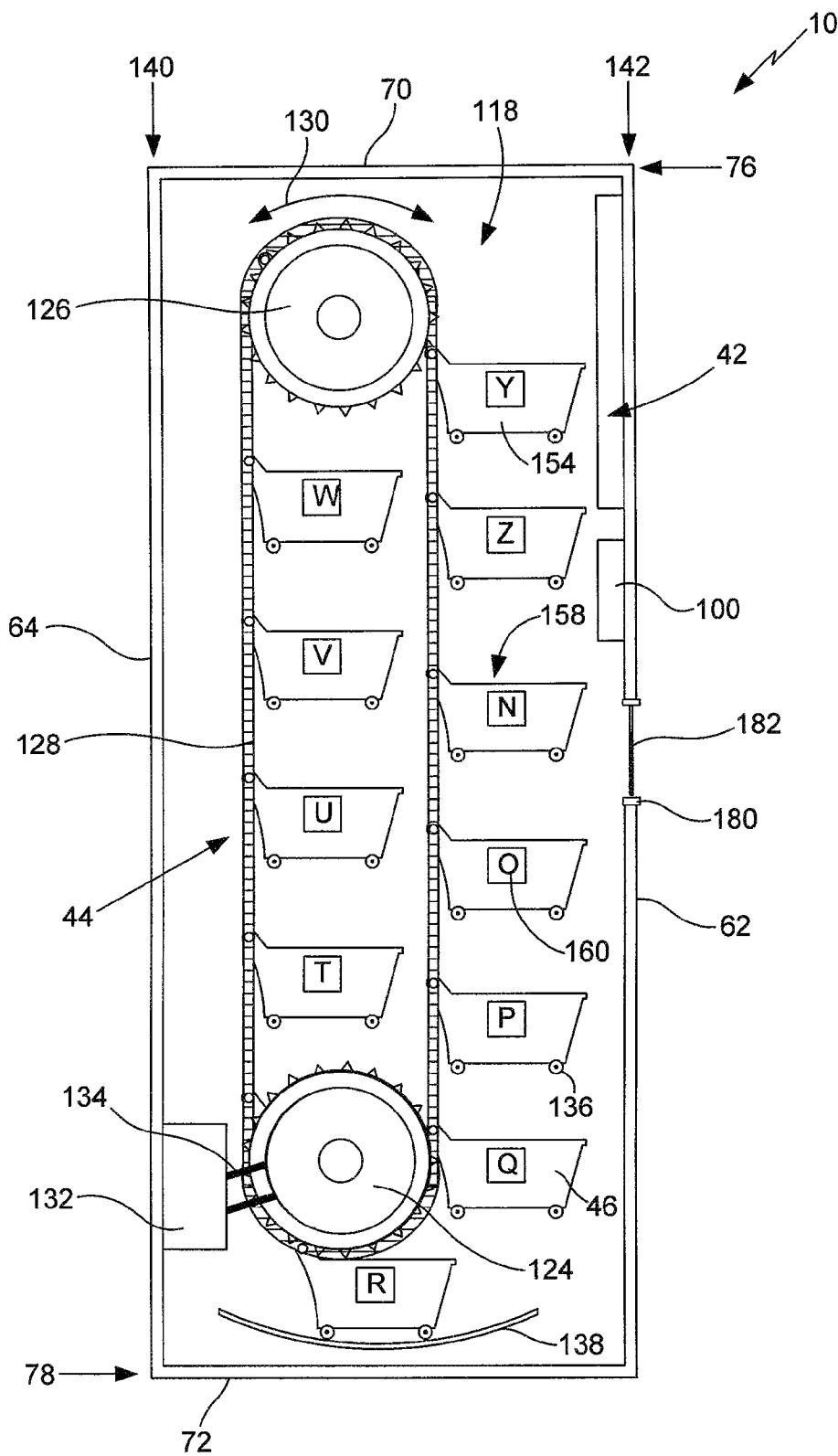
FIG. 16 is a side view of the apparatus of FIG. 15.

A third embodiment of the present invention is shown in FIGS. 15 and 16. In this embodiment, apparatus 10 comprises one or more access apertures 180 at the front side 142 of the housing 36, typically in the doors 38 (as shown) or the front wall 62 (as with the embodiment of FIG. 3). A flap member 182 is pivotally associated with the access apertures 180 to keep the access apertures 180 closed unless a customer 26 is accessing the medication through the access apertures 180. After the customer 26 confirms his or her identity using the display screen 90 and/or keypad 92, the conveying assembly 44 moves the appropriate bin 46 to a position generally behind the appropriate access aperture 180 (i.e., the one associated with patient's last name). In this embodiment, the bin 46 behind the access aperture 180 becomes the prescription tray 54. After the prescription identification system 50 confirms that the appropriate bin 46 is in place as the prescription tray 54, the customer 26 reaches through the access aperture 180, by pushing aside the flap 182, to the prescription tray 54 (the positioned bin 46) and grabs the package 48 having the prescription medication 14 and pulls the package 48 forward out of the interior 40 of the apparatus 10. The prescription identification system 50 will ensure that the customer 26 only grabs the proper package 48. In a preferred embodiment, the bins 46 will have wire or other dividers that separate the packages 48 in the bin 46 and to keep the packages 48 standing generally upright so the electronic tags 166 can be easily read by the prescription identification system 50. If the customer 26 does grab the improper package 48 and attempts to remove it from the apparatus 10, the alarm mechanism 110 can activate to audibly broadcast a loud siren or other sound letting the pharmacist 16 or employees 28 know that an improper package 48 was disturbed.

Figure 17:
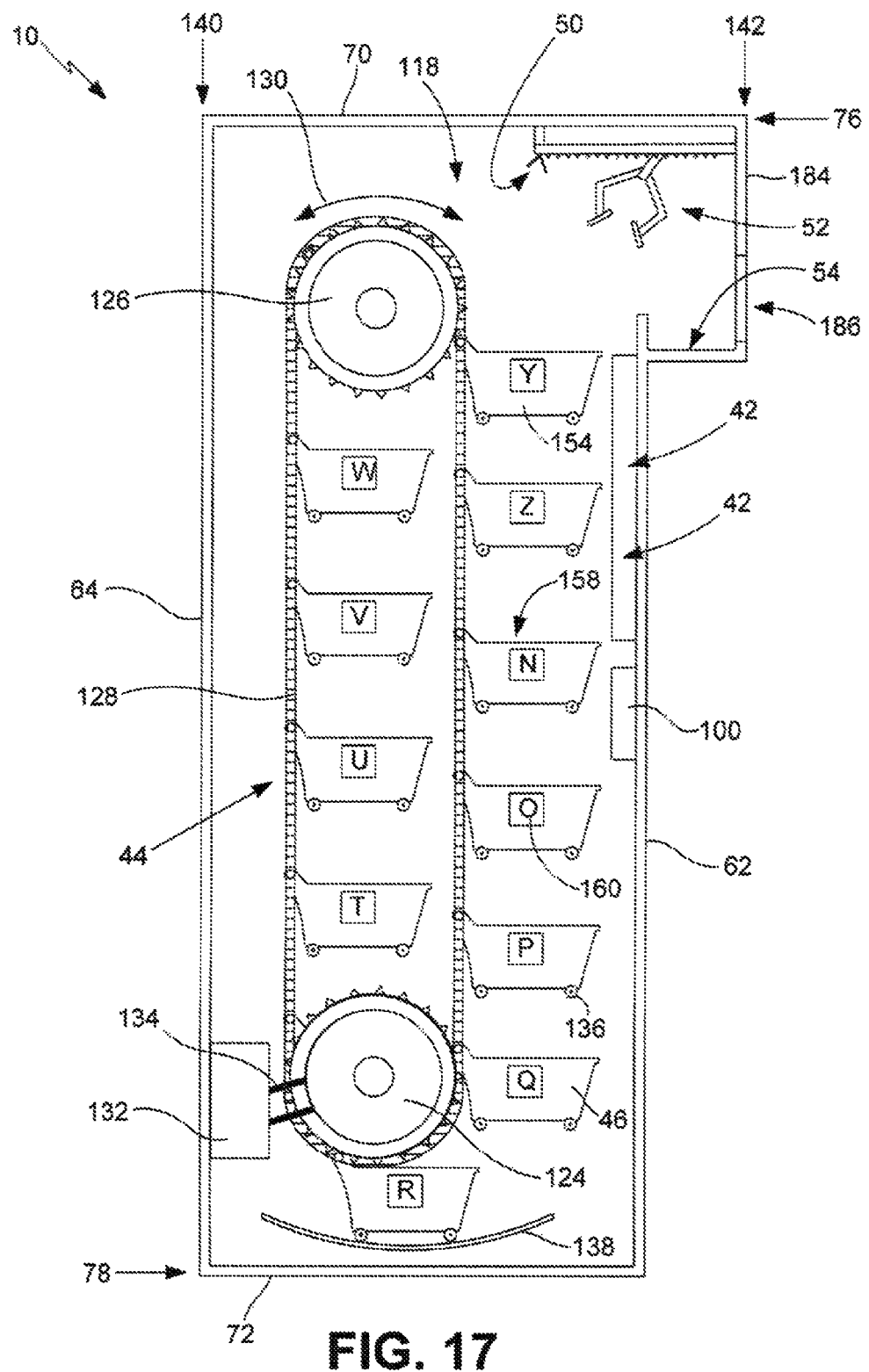
FIG. 17 is a side view of the fourth embodiment of the apparatus of the present invention showing use of an extension housing having an opening therein for retrieving the prescription medication.

A fourth embodiment of the apparatus 10 of the present invention is shown in FIG. 17. In this embodiment, the apparatus 10 includes an extension housing 184 that is integral with or mounted to the housing 26, using bolts, screws, rivets or like connectors, at the top end 76 thereof to provide grabbing mechanism 52 and a separate prescription tray 54. The extension housing 184, having the grabbing mechanism 52 and prescription tray 54, associated therewith is provided as an add-on or optional feature to the apparatus set forth in FIGS. 15 and 16. If desired, the flap 182 can be removed and the access aperture 180 can be closed off. With the extension housing 184, the grabbing mechanism 52 will work as set forth above, except positioned generally above most of the conveying assembly 44, to grab the appropriate package 48 containing the prescription medication 14 and place the package 48 on the prescription tray 54. The extension housing 184 can have an opening 186 associated therewith, either on the front or sides of the extension housing 184, through which the customer 26 can retrieve the package 48 having the prescription medication 14.

While there are shown and described herein specific forms of the invention, it will be readily apparent to those of ordinary skill in the art that the invention is not so limited, but instead is susceptible to various modifications and rearrangements in design and materials without departing from the spirit and scope of the invention. The embodiments described herein and shown in the figures were chosen in order to best explain the principles of the present invention. In particular, it should be noted that the present invention is subject to modification with regard to any dimensional relationships set forth herein and modifications in assembly, materials, size, shape and use. For instance, there are numerous components described herein that can be replaced with equivalent functioning components to accomplish the objectives of the present invention.

What is claimed is:

1. An apparatus for storing and dispensing prescription medication in a package after the prescription medication has been prepared by a pharmacist or an employee of a pharmacy, said apparatus comprising:

a housing having a front side, a back side, top end, bottom end, a first side and a second side with at least a front wall at said front side, a first side wall at said first side, a second side wall at said second side and a top wall at said top end, said housing defining an interior area therein;

a conveying assembly disposed in said interior area of said housing, said conveying assembly comprising a plurality of bins moveably disposed inside said interior of said housing so as to move along a conveying path, each of said bins having a compartment to receive the package containing the prescription medication;

one or more doors at one of said front side or said back side of said housing, said one or more doors configured to allow the pharmacist or the employee to access said interior area of said housing and place the package having the prescription medication on one of said plurality of bins in said interior area of said housing;

a prescription identification system disposed in said interior area of said housing, said prescription identification system associated with said conveying assembly so as to controllably position one of said plurality of bins;

a grabbing mechanism structured and arranged to remove the package containing the prescription medication from one of the plurality of bins and place the package in a prescription tray, said grabbing mechanism and said prescription tray disposed in an extension housing extending outward of said front side of said housing, said extension housing having an opening therein to allow the customer to access the package on said prescription tray; and a customer access panel at said front side of said housing, said customer access panel comprising at least a computer and one of a display screen and a keypad electronically connected to said computer, said customer access panel configured to operate said conveying assembly so as to move the prescription medication to said prescription tray so the prescription medication may be retrieved by a customer of the pharmacy.

2. The apparatus claim 1, wherein said one or more doors are at said back side of said housing and said housing is disposed in a wall of said pharmacy with said front side of said housing at or extending forward of said wall.

3. The apparatus of claim 1, wherein said prescription tray opens outward of said housing to allow the customer to access said prescription tray for removing the prescription medication from the apparatus.

4. The apparatus of claim 1, wherein said grabbing mechanism comprises a grabbing conveyor supported by said extension housing and a grabbing device configured to be moved by said grabbing conveyor to said one of said plurality of bins having the package containing the prescription medication.

5. The apparatus of claim 1, wherein said customer access panel further comprises at least one of a printer having a paper slot associated therewith, a card reader with a card slot associated therewith, a camera, a thumb print reader, an alarm mechanism, a speaker and a microphone.

6. The apparatus of claim 1, wherein said customer access panel comprises a motion detector configured to detect a customer approaching said apparatus so as to activate said display screen.

7. The apparatus of claim 1, wherein said conveying assembly comprises a lower socket toward the lower end of said housing, an upper socket toward the top end of said housing, a drive chain interconnecting said lower socket and said upper socket and a motor operatively connected to at least one of said lower socket and said upper socket, each of said plurality of bins operatively connected to said drive chain so as to support said bins to prevent the prescription medication from falling out of said compartment thereof.

8. The apparatus of claim 1, wherein said conveying assembly comprises a first subassembly and a second subassembly, each of said first subassembly and said second subassembly comprising a plurality of bins.

9. The apparatus of claim 1, wherein said prescription identification system is comprises an electronic reader configured to detect and read identifier tags on each of said bins and an electronic tag on the package containing the prescription medication.

10. An apparatus for storing and dispensing prescription medication in a package after the prescription medication has been prepared by a pharmacist or an employee of a pharmacy, said apparatus comprising:

a housing having a front side, a back side, top end, bottom end, a first side and a second side with at least a front wall at said front side, a first side wall at said first side, a second side wall at said second side and a top wall at said top end, said housing defining an interior area therein;

a conveying assembly disposed in said interior area of said housing, said conveying assembly comprising a plurality of bins moveably disposed inside said interior of said housing so as to move along a conveying path, each of said bins having a compartment to receive the package containing the prescription medication;

one or more doors at one of said front side or said back side of said housing, said one or more doors configured to allow the pharmacist or the employee to access said interior area of said housing and place the package having the prescription medication on one of said plurality of bins in said interior area of said housing;

a grabbing mechanism disposed in said housing, said grabbing mechanism structured and arranged to remove the package containing the prescription medication from one of said plurality of bins and place the package in a prescription tray accessible by a customer of the pharmacy, said grabbing mechanism comprising a grabbing device configured to grab the package in said one of said plurality of bins, said grabbing mechanism and said prescription tray disposed in an extension housing extending outward of said front side of said housing, said extension housing having an opening therein to allow the customer to access the package on said prescription tray;

a prescription identification system disposed in said interior area of said housing, said prescription identification system associated with each of said conveying assembly and said grabbing mechanism so as to controllably position one of said plurality of bins and to remove the package from said one of said plurality of bins, said prescription identification system having an electronic reader configured to detect and read identifier tags on each of said bins and an electronic tag on the package containing the prescription medication; and a customer access panel associated with said housing, said customer access panel comprising at least a computer and one of a display screen and a keypad electronically connected to said computer, said customer access panel configured to operate said conveying assembly and said grabbing mechanism so as to move the prescription medication to said prescription tray so the prescription medication may be retrieved by the customer of the pharmacy.

11. The apparatus of claim 10, wherein said prescription tray opens outward of said housing to allow the customer to access said prescription tray for removing the prescription medication from the apparatus.

12. The apparatus of claim 10, wherein said conveying assembly comprises a lower socket toward the lower end of said housing, an upper socket toward the top end of said housing, a drive chain interconnecting said lower socket and said upper socket and a motor operatively connected to at least one of said lower socket and said upper socket, each of said plurality of bins operatively connected to said drive chain so as to support said bins to prevent the prescription medication from falling out of said compartment thereof.

13. A method for storing, dispensing and obtaining prescription medication in a package after the prescription medication has been prepared by a pharmacist or an employee of a pharmacy, said method comprising the steps of:

(a) a customer of a pharmacy approaching an apparatus comprising a housing enclosing an interior area with a conveying assembly disposed therein, said conveying assembly having a plurality of bins with the package containing the prescription medication on one of said plurality of bins, the apparatus further comprising a prescription identification system disposed in said interior area of said housing and a customer access panel at a front side of said housing, said prescription identification system associated with said conveying assembly so as to controllably position one of said plurality of bins and to facilitate removal of the package from said one of said plurality of bins, said customer access panel comprising at least a computer and one of a display screen and a keypad electronically connected to said computer, said customer access panel configured to operate said conveying assembly to move the package to a prescription tray so the package may be retrieved by the customer, said prescription tray disposed in an extension housing extending outward of said front side of said housing, said prescription tray being accessible by the customer of the pharmacy through an opening in said extension housing;

(b) confirming the identity of the customer to connect the customer with the package containing the prescription medication;

(c) activating said conveying assembly and said prescription identification system to move said plurality of bins and position said one of said plurality of bins having said package so said package can be retrieved by the customer on said prescription tray;

(d) grabbing said package and placing the package on said prescription tray, said grabbing step accomplished by a grabbing mechanism disposed in said extension housing, said grabbing mechanism operatively associated with said prescription identification system so as to locate and grab the package, said grabbing mechanism structured and arranged to remove the package containing the prescription medication from said one of said plurality of bins and place the package on said prescription tray, said grabbing mechanism comprising a grabbing device configured to grab the package in said one of said plurality of trays; and (e) retrieving said package from said prescription tray by the customer.

14. The method of claim 13, wherein said prescription identification system is associated with said conveying assembly so as to controllably position said one of said plurality of bins and to allow removal of the package from said one of said plurality of bins by said grabbing device, said prescription identification system having an electronic reader configured to detect and read identifier tags on each of said bins and an electronic tag on the package containing the prescription medication.

* * * * *